United States Patent
Okuda et al.

(10) Patent No.: US 7,880,109 B2
(45) Date of Patent: Feb. 1, 2011

(54) CLASSIFICATION APPARATUS AND FINE PARTICLE MEASURING APPARATUS

(75) Inventors: Daiji Okuda, Kyoto (JP); Hiroshi Okuda, Kyoto (JP); Fujio Inoue, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 197 days.

(21) Appl. No.: 12/158,650

(22) PCT Filed: Dec. 22, 2006

(86) PCT No.: PCT/JP2006/325593

§ 371 (c)(1),
(2), (4) Date: Jun. 20, 2008

(87) PCT Pub. No.: WO2007/072942

PCT Pub. Date: Jun. 28, 2007

(65) Prior Publication Data

US 2009/0173670 A1    Jul. 9, 2009

(30) Foreign Application Priority Data

Dec. 22, 2005 (JP) .............................. 2005-369776

(51) Int. Cl.
*B03C 7/00* (2006.01)
(52) U.S. Cl. .................. 209/129; 209/12.2; 209/154
(58) Field of Classification Search ............ 209/12.2, 209/127.1, 129, 147, 154, 551, 906
See application file for complete search history.

(56) References Cited

U.S. PATENT DOCUMENTS 3,526,828 A * 9/1970 Whitby ....................... 324/464

(Continued)

FOREIGN PATENT DOCUMENTS

JP    2000-046720 A    2/2000

(Continued)

OTHER PUBLICATIONS

International Search Report for the Application No. PCT/JP2006/325593 mailed Apr. 3, 2007.

*Primary Examiner*—Joseph C Rodriguez
(74) *Attorney, Agent, or Firm*—Cheng Law Group, PLLC

(57) ABSTRACT

A classification apparatus for classifying and separating particles having particle sizes within a predetermined range is disclosed. In a preferred embodiment of the classification apparatus, a center electrode (3) and an outside electrode (4) generate an electric field for classifying charged fine particles according to electric mobility. In the upper part of a housing (1), a sheath gas supply portion (7) is provided. An aerosol supply portion (11) has an introduction port (11*a*) provided on the outside electrode (4) side in a classification region (5), and supplies a charged aerosol at a constant flow rate through the introduction port (11*a*). On the downstream side in the flow of a sheath gas in the classification region (5), a larger-size particle discharge portion (13) is provided. The larger-size particle discharge portion (13) has a discharge port (13*a*) provided on the outside electrode (4) side, and discharges charged fine particles, which are contained in the classified charged aerosol and have particle sizes larger than a predetermined particle size, together with part of the sheath gas at a constant flow rate. A detector (18) is provided downstream of the housing (1) to detect the number of remaining charged fine particles contained in the sheath gas introduced thereinto as the quantity of electricity.

13 Claims, 15 Drawing Sheets

U.S. PATENT DOCUMENTS

| | | | |
|---|---|---|---|
| 4,769,609 A * | 9/1988 | Masuda | 324/455 |
| 6,003,389 A * | 12/1999 | Flagan et al. | 73/865.5 |
| 6,230,572 B1 * | 5/2001 | Pui et al. | 73/863.21 |
| 6,498,313 B1 * | 12/2002 | Stencel et al. | 209/131 |
| 6,892,142 B2 * | 5/2005 | Takeuchi et al. | 702/23 |
| 7,145,320 B2 * | 12/2006 | Yoshida et al. | 324/71.4 |
| 7,213,476 B2 * | 5/2007 | Cheng et al. | 73/865.5 |
| 7,416,902 B2 * | 8/2008 | Pletcher et al. | 436/174 |
| 2008/0029440 A1 * | 2/2008 | Blanchard | 209/127.1 |

FOREIGN PATENT DOCUMENTS

| | | |
|---|---|---|
| JP | 3459359 B2 | 10/2003 |
| JP | 2005-024409 A | 1/2005 |
| JP | 2005-214931 A | 8/2005 |

* cited by examiner

Fig. 4C

SHEATH GAS FLOW RATE 100[L/min]

AEROSOL GAS INTRODUCTION PORT

DISCHARGE PORT

SHEATH GAS FLOW RATE 100[L/min]

EMISSION GAS

120nm
100nm

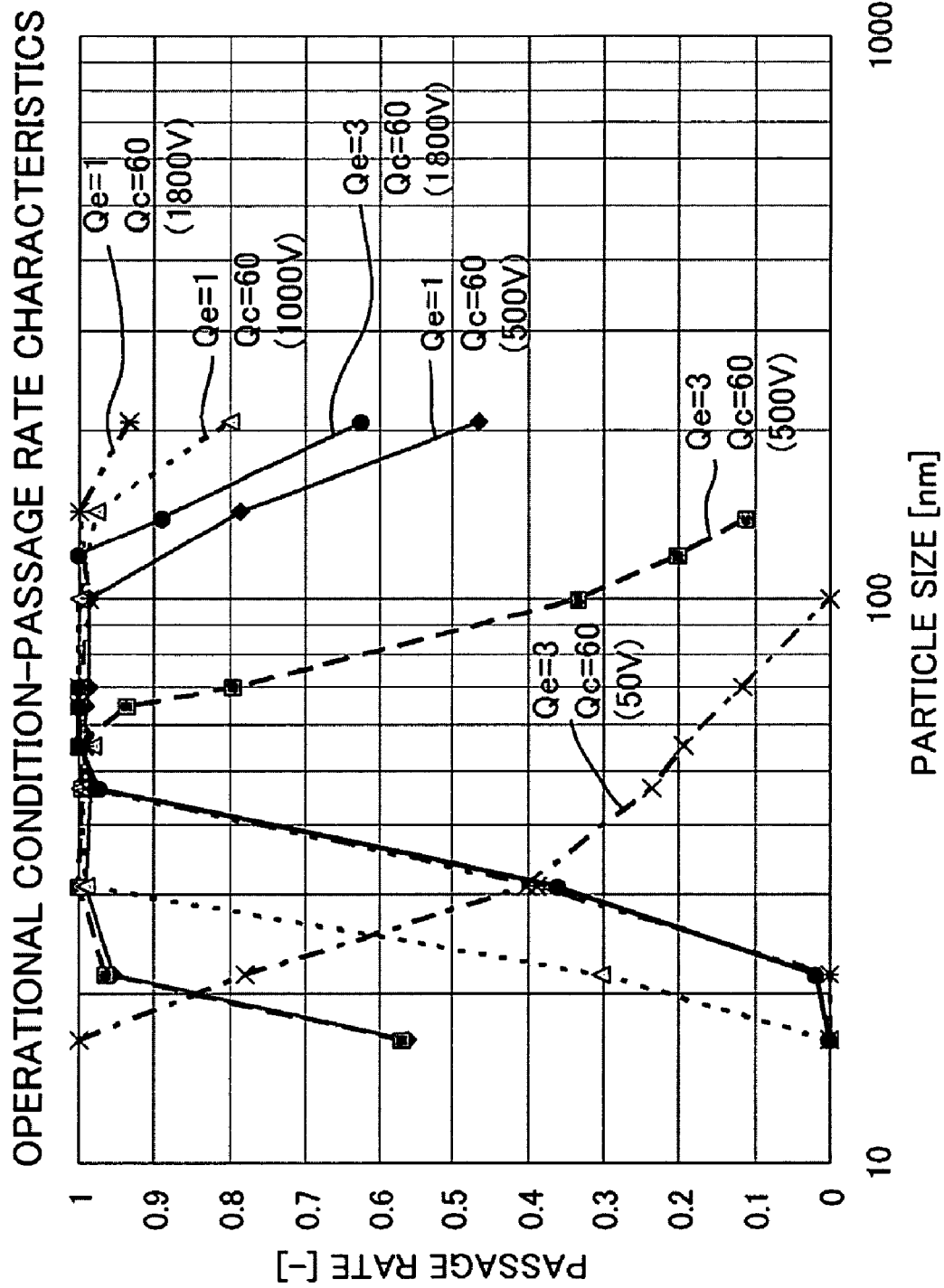

Fig. 8A
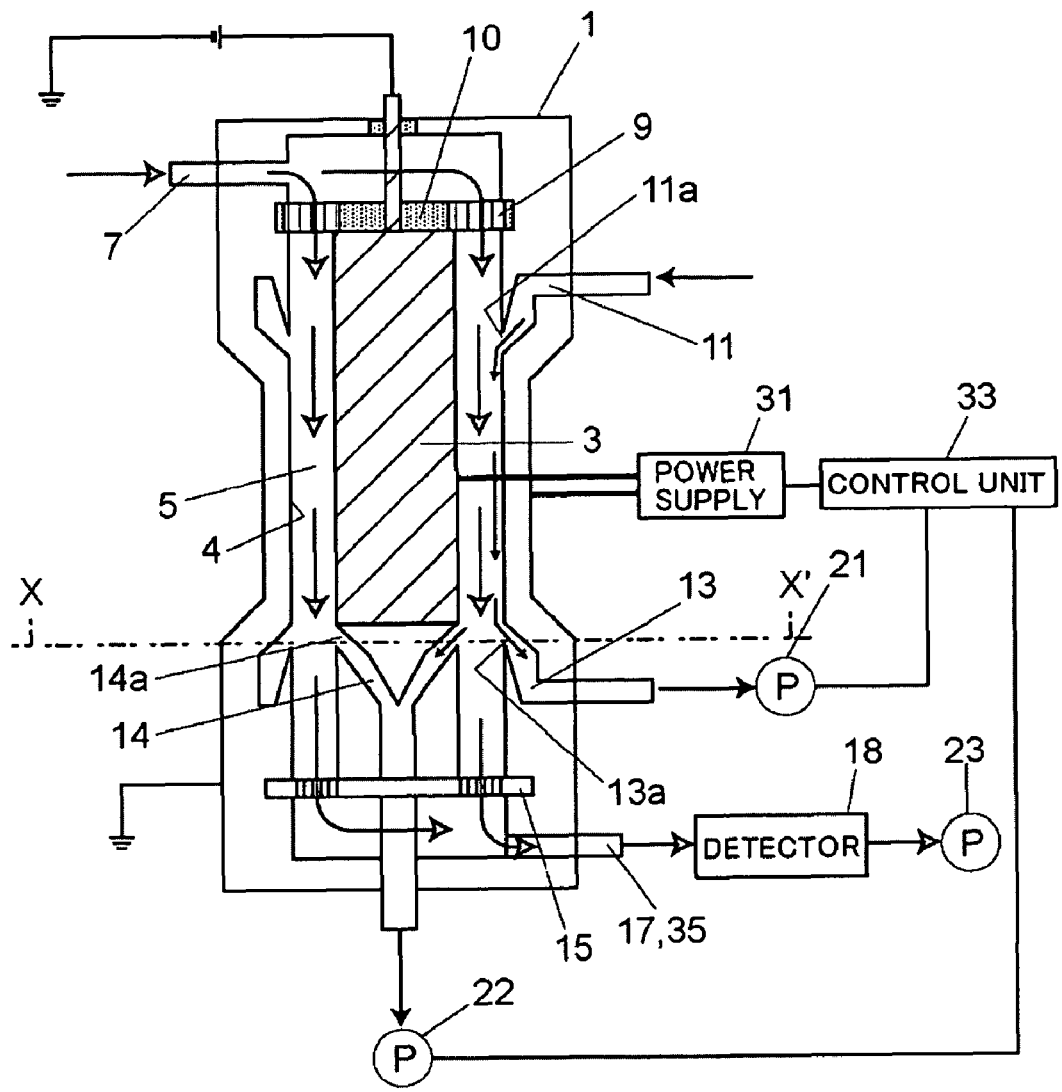
Fig. 8B
Fig. 8C
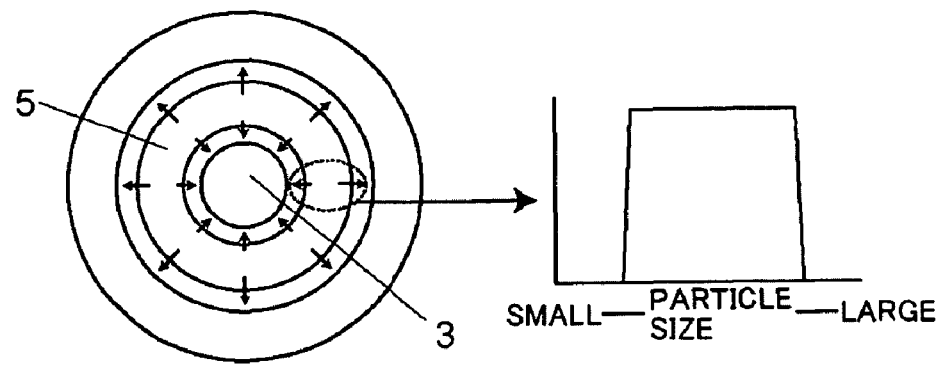

CLASSIFICATION APPARATUS AND FINE PARTICLE MEASURING APPARATUS

TECHNICAL FIELD

The present invention relates to a classification apparatus for separating fine particles, having particle sizes within a predetermined range, from environmental gas, and an apparatus for measuring the number of fine particles separated by the classification apparatus, for example, an apparatus for measuring the number of fine particles contained in car exhaust in real time.

BACKGROUND ART

An aerosol is generally a colloid in which a solid or liquid as a dispersoid is dispersed in a gas as a dispersion medium, and examples of such an aerosol include car exhaust.

As an apparatus for classifying fine particles contained in an aerosol as a measuring object, an apparatus designed to electrically charge an aerosol and classify charged fine particles contained in the aerosol by utilizing the difference in their mobility in an electric field is known. As an apparatus for measuring fine particles, an electric mobility analyzer designed to measure the electric mobility of classified fine particles is known. There is a certain relationship between the electric mobility and the particle size of a fine particle, and therefore by specifying an electric mobility, it is possible to specify a particle size.

Electric mobility analyzers are divided into two types: differential mobility analyzers (DMA) (see Patent document 1) capable of separating fine particles having a certain electric mobility and electric mobilities in its immediate vicinity, and integral mobility analyzers capable of separating fine particles having electric mobilities less than a certain electric mobility.

The particle size distribution of fine particles contained in car exhaust generally has two characteristic modes, a nuclei mode and an accumulation mode. The particle size distribution of nuclei mode particles has a peak of about 10 nm, and the particle size distribution of accumulation mode particles has a peak of about 70 nm and ranges from about 30 to 100 nm. The nuclei mode particles and accumulation mode particles are different in generation mechanism and composition, and therefore need to be separated from each other to measure both of the total number of nuclei mode particles and the total number of accumulation mode particles in real time.

In order to measure accumulation mode particles, a measuring apparatus needs to have such passage characteristics that it passes fine particles having particle sizes in the range of, for example, 30 to 100 nm at a constant passage rate but does not pass fine particles having particle sizes smaller than 30 nm and fine particles having particle sizes larger than 100 nm.

Patent document 1: Japanese Patent No. 3459359

DISCLOSURE OF THE INVENTION

Problems to be Solved by the Invention

Even when a conventional differential mobility analyzer is used, trapezoidal passage characteristics allowing particles having particle sizes within a wide range to pass through the analyzer can be obtained by changing the flow-rate ratio among a sheath gas, an aerosol gas and a gas to be detected (i.e., a gas to be introduced into a particle counter). However, the particle size range of particles which can pass through such a conventional differential mobility analyzer is as narrow as, for example, from 80 to 100 nm, and therefore it is difficult to measure or separate particles having particle sizes within a wide range, such as accumulation mode particles having particle sizes in the range of, for example, 30 to 100 nm, at a time.

It is therefore an object of the present invention to provide a classification apparatus capable of classifying and separating fine particles, having particle sizes within a predetermined range, from an aerosol and a measuring apparatus capable of measuring the number of particles, separated by the classification apparatus and having particle sizes within an aerosol particle size range, at a time.

Means for Solving the Problems

In order to achieve the above object, the present invention is directed to a classification apparatus for classifying fine particles having particle sizes within a wide range based on fundamental principles of an electric mobility analyzer. The classification apparatus according to the present invention includes: a pair of electrodes opposed to each other to generate an electric field for classifying charged fine particles according to electric mobility to form a classification region; a sheath gas supply portion for supplying a non-charged gas as a sheath gas to the classification region from one end of the classification region; an aerosol supply portion which has an introduction port provided in one of the electrodes or its vicinity and supplies a charged aerosol through the introduction port; a larger-size particle discharge portion which has a discharge port provided in the one of the electrodes or its vicinity on the downstream side in the sheath gas flow and discharges charged fine particles, which are contained in the classified charged aerosol and have particle sizes larger than a predetermined particle size, together with part of the sheath gas; and an outlet provided on the other end side of the classification region to discharge remaining charged fine particles together with the sheath gas.

One method for keeping a constant particle size distribution range when charged fine particles, which are contained in the classified charged aerosol and have particle sizes larger than a predetermined particle size, are discharged together with part of the sheath gas is keeping the flow rate of a gas discharged through the discharge port constant.

The phrase "its vicinity" refers to a position located on the same side as and near one of the electrodes. More specifically, in the case of the introduction port of the aerosol supply portion, the phrase "its vicinity" means a position allowing the introduction port to perform the function of supplying the charged aerosol to the classification region, and in the case of the discharge port of the larger-size particle discharge portion, the phrase "its vicinity" means a position allowing the discharge port to perform the function of discharging fine particles, which are contained in the classified charged aerosol and have particle sizes larger than a predetermined particle size, together with part of the sheath gas.

The term "charged aerosol" refers to an aerosol supplied to the classification apparatus through a charging device. The charged aerosol contains charged fine particles and non-charged fine particles. The ratio of charged fine particles to the total fine particles contained in an aerosol, which has not yet been passed through the charging device, is referred to as a charging rate.

The present invention is intended to separate fine particles having particle sizes within a predetermined range by removing not only charged fine particles having particle sizes larger than the predetermined range but also charged fine particles having particle sizes smaller than the predetermined range from charged fine particles contained in an aerosol having a particle size distribution, or to determine the number of fine particles having particle sizes within a predetermined range.

Therefore, the classification apparatus according to the present invention preferably further includes a particle size selecting means whereby the particle size distribution range of charged fine particles to be discharged through the outlet can be adjusted.

The particle size selecting means is a means for selecting particle size distribution range by controlling the flow rate of a gas discharged through the larger-size particle discharge portion and/or a voltage applied between the electrodes opposed to each other. The phrase "and/or" used here means that a particle size distribution range is selected by controlling one or both of the gas flow rate and the voltage.

One example of the particle size selecting means is one which controls the flow rate of a pump connected downstream of the larger-size particle discharge portion to discharge charged fine particles, having particle sizes larger than a predetermined particle size, together with part of the sheath gas. In this case, when the flow rate of the pump is increased, the particle size range of charged particles to be discharged through the discharge port is widened on the large particle size side so that a wide range of charged particles distributed on the large particle size side are removed from charged particles to be discharged through the outlet. On the other hand, when the flow rate of the pump is reduced, the particle size range of particles to be discharged through the discharge port is not widened on the large particle size side so that a narrow range of charged particles distributed on the large particle size side are removed from charged particles to be discharged through the outlet.

Another example of the particle size selecting means is one which controls a power supply connected to the electrodes opposed to each other to adsorb charged fine particles, having particle sizes smaller than a predetermined particle size, to the electrode. In this case, when a voltage applied between the electrodes opposed to each other is increased, the particle size range of charged fine particles to be adsorbed to the electrode is widened on the small particle size side so that a wide range of charged fine particles distributed on the small particle size side are removed from charged fine particles to be discharged through the outlet. On the other hand, when a voltage applied between the electrodes opposed to each other is reduced, the particle size range of charged fine particles to be adsorbed to the electrode is not widened on the small particle size side so that a narrow range of charged fine particles distributed on the small particle size side are removed from charged fine particles to be discharged through the outlet.

In this way, fine particles having particle sizes larger than a predetermined range are removed by the larger-size particle discharge portion, and fine particles having particle sizes smaller than the predetermined range are classified in the classification region and then removed by being attracted and adsorbed to the other of the electrodes.

The particle size range of fine particles to be removed by the larger-size particle discharge portion and the particle size range of fine particles to be removed by being adsorbed to the other electrode can be set by adjusting the flow rate of a sheath gas supplied to the classification region (Qc), the flow rate of a charged aerosol gas supplied from the aerosol supply portion through the introduction port to the classification region (Qa), the flow rate of a gas discharged through the larger-size particle discharge portion (Qe), and a voltage applied between the electrodes opposed to each other. Such particle size ranges of particles to be removed can be adjusted while the particle size distribution of a gas to be introduced into a detector connected to the outlet is measured by introducing the gas into a conventional differential mobility analyzer.

In order to further reliably remove fine particles having particle sizes smaller than a predetermined particle size range, the classification apparatus according to the present invention may further include a smaller-size particle discharge portion which has a discharge port provided in the other electrode or its vicinity on the downstream side in the sheath gas flow and discharges charged fine particles, which have particle sizes smaller than a predetermined particle size but have not been adsorbed to the electrode, together with part of the sheath gas through the discharge port. In a case where the smaller-size particle discharge portion is provided to remove fine particles having particle sizes smaller than a predetermined particle size range, the above-described method for removing fine particles having particle sizes smaller than a predetermined particle size range by adsorbing them to the electrode may be used together, or one of the methods may be used singly. It is to be noted that by using these methods together, it is possible to further reliably remove fine particles having particle sizes smaller than a predetermined particle size range.

The phrase "its vicinity" used for explaining the position of the discharge port of the smaller-size particle discharge portion refers to a position located on the same side as and near the other electrode, more specifically, a position allowing the discharge port to perform the function of discharging charged fine particles, which are contained in the classified charged aerosol and have particle sizes smaller than a predetermined particle size, together with part of the sheath gas.

The particle size selecting means may control the flow rate of a pump connected downstream of the discharge port of the smaller-size particle discharge portion to control the particle size range of fine particles to be discharged through the outlet. In this case, when the flow rate of the pump is increased, the particle size range of charged particles to be discharged through the discharge port is widened on the small particle size side so that a wide range of charged particles distributed on the small particle size side are removed from charged fine particles to be discharged through the outlet. On the other hand, when the flow rate of the pump is reduced, the particle size range of charged particles discharged through the discharge port is not widened on the small particle size side so that a narrow range of charged particles distributed on the small particle size side are removed from charged particles to be discharged through the outlet.

When classified charged fine particles are attached to the wall surface and the like of the classification apparatus, there is a case where they are not discharged through the outlet and therefore cannot be accurately collected. Therefore, a pair of converging electrodes may be provided to be opposed to each other in an area between the classification region and the outlet to generate an electric field opposite in direction to that generated by the electrodes for forming a classification region so that classified charged fine particles are converged and led to the outlet.

Further, in order to lead only charged fine particles converged by the converging electrodes to a detector, that is, in order to prevent part of the sheath gas not containing charged fine particles from being led to a detector, an outlet slit may be provided between the converging electrodes and the outlet to selectively lead charged fine particles converged by the converging electrodes to the outlet together with part of the sheath gas.

A preferred example of the detector is a Faraday cup electrometer for measuring the number of charged fine particles as the quantity of electricity.

The present invention is also intended to remove not only fine particles having particle sizes larger than a predetermined range but also fine particles having particle sizes smaller than the predetermined range from an aerosol having a particle size distribution to measure fine particles having particle sizes within the predetermined range.

Therefore, the present invention is also directed to a fine particle measuring apparatus including: the classification apparatus according to the present invention; and a detector provided downstream of the outlet to detect the number of remaining particles contained in the sheath gas introduced thereinto.

In the fine particle measuring apparatus, converging electrodes may be provided in an area between the classification region and the outlet to be opposed to each other to generate an electric field opposite in direction to that generated by the electrodes for forming a classification region to converge classified charged fine particles and lead them to the outlet. Although it is necessary to use a large detector to directly detect all the classified charged fine particles, the use of such converging electrodes makes it possible to reduce the size of the detector.

Further, an outlet slit may be provided to lead only charged fine particles converged by the converging electrodes to the detector. This makes it possible to reduce the flow rate of the sheath gas to be introduced into the detector, thereby further reducing the size of the detector.

A physical quantity that should be finally determined by the fine particle measuring apparatus according to the present invention is the number of fine particles which are contained in an aerosol not electrically charged and have particle sizes within a predetermined range, but an output obtained by the detector is the quantity of electricity corresponding to the number of charged fine particles contained in the charged aerosol. Therefore, it is necessary to convert an output obtained by the detector into the number of fine particles contained in the aerosol not electrically charged. This calculation can be performed using the charging rate of the aerosol as a measuring object previously determined by charging the aerosol with the use of a charging device in the measuring apparatus. In order to automatically perform this calculation, the measuring apparatus preferably has a data processing unit which retains the previously-determined charging rate of an aerosol as a measuring object and calculates the fine particle number concentration of the measured aerosol based on the quantity of electricity measured by the detector.

The "charging rate" of an aerosol can be determined from the ratio between the total number of fine particles contained in a non-charged aerosol and the total number of fine particles contained in the charged aerosol from which charged fine particles have been removed. Removal of charged fine particles from a charged aerosol can be carried out by allowing the charged aerosol to pass through an electric field. The total number of fine particles contained in a non-charged aerosol can be determined using, for example, a particle counter utilizing light scattering.

By providing such a data processing unit which retains the charging rate of an aerosol and calculates the particle number concentration of the measured aerosol based on the quantity of electricity measured by the detector, it is possible to automatically determine the particle number concentration of the aerosol online.

EFFECT OF THE INVENTION

The classification apparatus according to the present invention includes a pair of electrodes opposed to each other, a sheath gas supply portion, an aerosol supply portion, and an outlet to classify charged fine particles contained in a charged aerosol based on fundamental principles of an electric mobility analyzer. Further, the classification apparatus according to the present invention includes a larger-size particle discharge portion to remove classified charged fine particles having particle sizes larger than a predetermined particle size. On the other hand, charged fine particles having particle sizes smaller than a predetermined particle size range are removed by allowing the other electrode to attract and adsorb them. Therefore, by using the classification apparatus according to the present invention, it is possible to separate fine particles, having particle sizes within a predetermined range, from a charged aerosol or to measure the total number of charged fine particles having particle sizes within a predetermined range.

The particle size range of fine particles to be discharged through the outlet and measured can be made sufficiently wide, for example, from 30 to 100 nm by setting the particle size ranges of fine particles to be removed by the larger-size particle discharge portion and the smaller-size particle discharge portion by adjusting any one of the flow rate of a sheath gas, the flow rate of a charged aerosol gas, the flow rate of a gas discharged through the larger-size particle discharge portion, and a voltage applied between the electrodes opposed to each other.

BRIEF DESCRIPTION OF THE DRAWINGS

FIG. 1A is a vertical sectional view schematically showing a classification apparatus according to one embodiment of the present invention.

FIG. 1B is a horizontal sectional view taken along the X-X' line in FIG. 1A.

FIG. 2A is a vertical sectional view schematically showing a fine particle measuring apparatus according to one embodiment of the present invention.

FIG. 2B is a horizontal sectional view taken along the X-X' line in FIG. 2A.

FIG. 3A is a simulation result showing the paths of charged fine particles having particle sizes of 100 nm and 120 nm, obtained by setting the flow rate of a sheath gas to 100 L/min, the flow rate of a gas discharged through a larger-size particle discharge portion 13 to 5.0 L/min, and the flow rate of an aerosol gas to 0.8 L/min.

FIG. 3B is a simulation result showing the paths of charged fine particles having particle sizes of 100 nm and 120 nm, obtained by setting the flow rate of a sheath gas to 100 L/min, the flow rate of a gas discharged through the larger-size particle discharge portion 13 to 5.0 L/min, and the flow rate of an aerosol gas to 0.9 L/min.

FIG. 3C is a simulation result showing the paths of charged fine particles having particle sizes of 100 nm and 120 nm, obtained by setting the flow rate of a sheath gas to 100 L/min, the flow rate of a gas discharged through the larger-size particle discharge portion 13 to 5.0 L/min, and the flow rate of an aerosol gas to 1.0 L/min.

FIG. 3D is a simulation result showing the paths of charged fine particles having particle sizes of 100 nm and 120 nm, obtained by setting the flow rate of a sheath gas to 100 L/min, the flow rate of a gas discharged through the larger-size particle discharge portion 13 to 5.0 L/min, and the flow rate of an aerosol gas to 1.1 L/min.

FIG. 4C is a simulation result showing the paths of charged fine particles having particle sizes of 20, 21, 22, 100, and 120 nm, obtained by setting the flow rate of an aerosol gas to 1.0 L/min, the flow rate of a gas discharged through the larger-size particle discharge portion 13 to 5.0 L/min, and the flow rate of a sheath gas to 100 L/min.

FIG. 4D is a view showing the paths of charged fine particles near a discharge port shown in FIG. 4C.

FIG. 7 is a graph showing the relationship between operational conditions and particle characteristics (passage rate characteristics), wherein the vertical axis represents the ratio of fine particles discharged through the outlet to fine particles contained in an aerosol supplied from an aerosol supply portion (passage rate) and the horizontal axis represents particle sizes (nm) of fine particles discharged through the outlet.

FIG. 8A is a vertical sectional view schematically showing a classification apparatus according to another embodiment of the present invention.

FIG. 8B is a horizontal sectional view taken along the X-X' line in FIG. 8A.

FIG. 8C is a schematic view showing a particle size distribution in an area surrounded by a broken line in FIG. 8B.

Figure 9A:
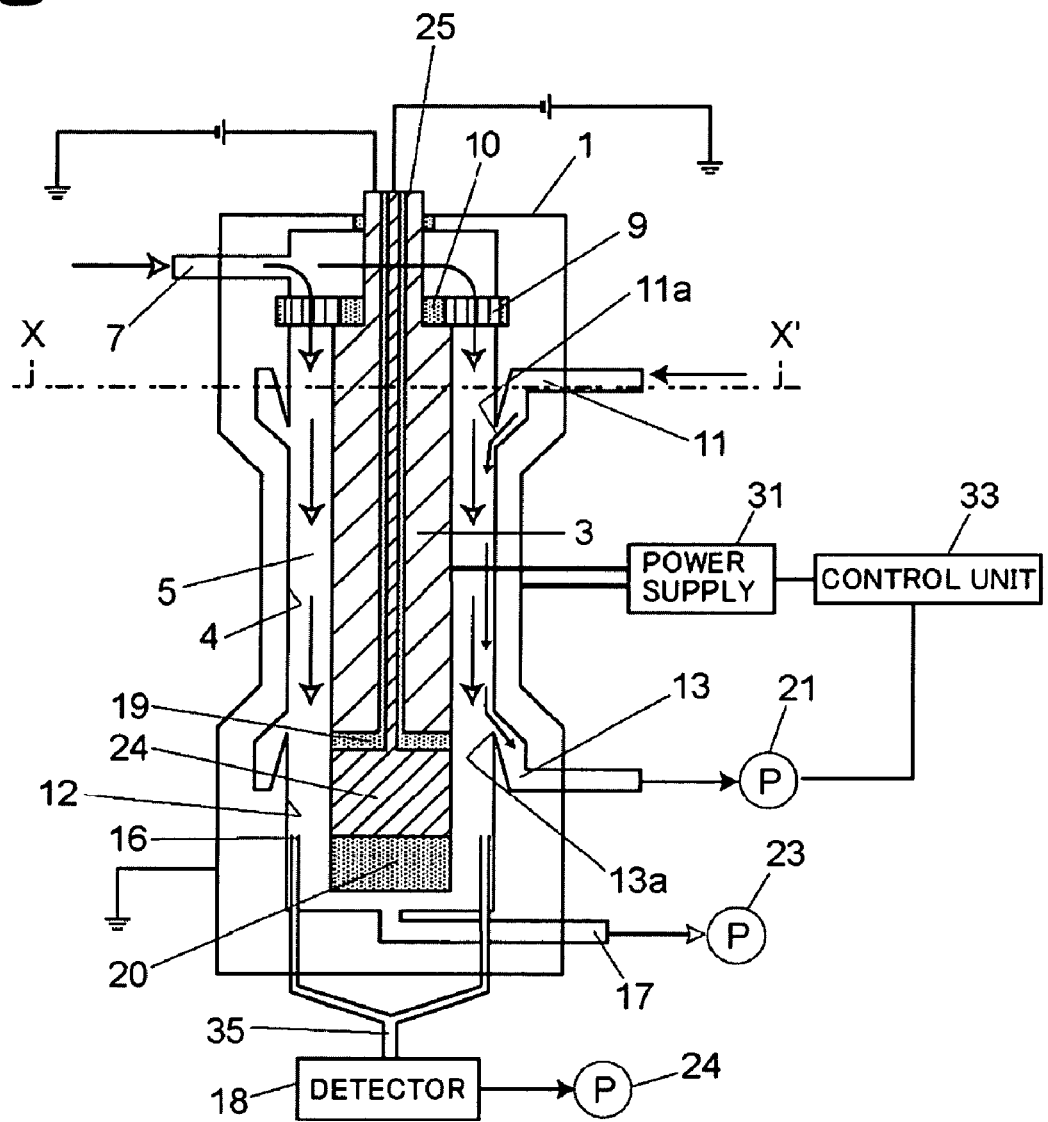

FIG. 9A is a vertical sectional view schematically showing a classification apparatus according to another embodiment of the present invention.

Figure 9B:
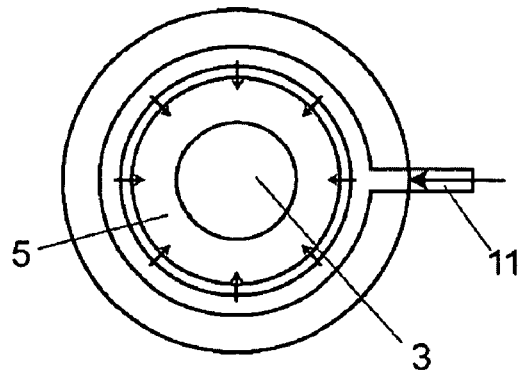

FIG. 9B is a horizontal sectional view taken along the X-X' line in FIG. 9A.

Figure 10:
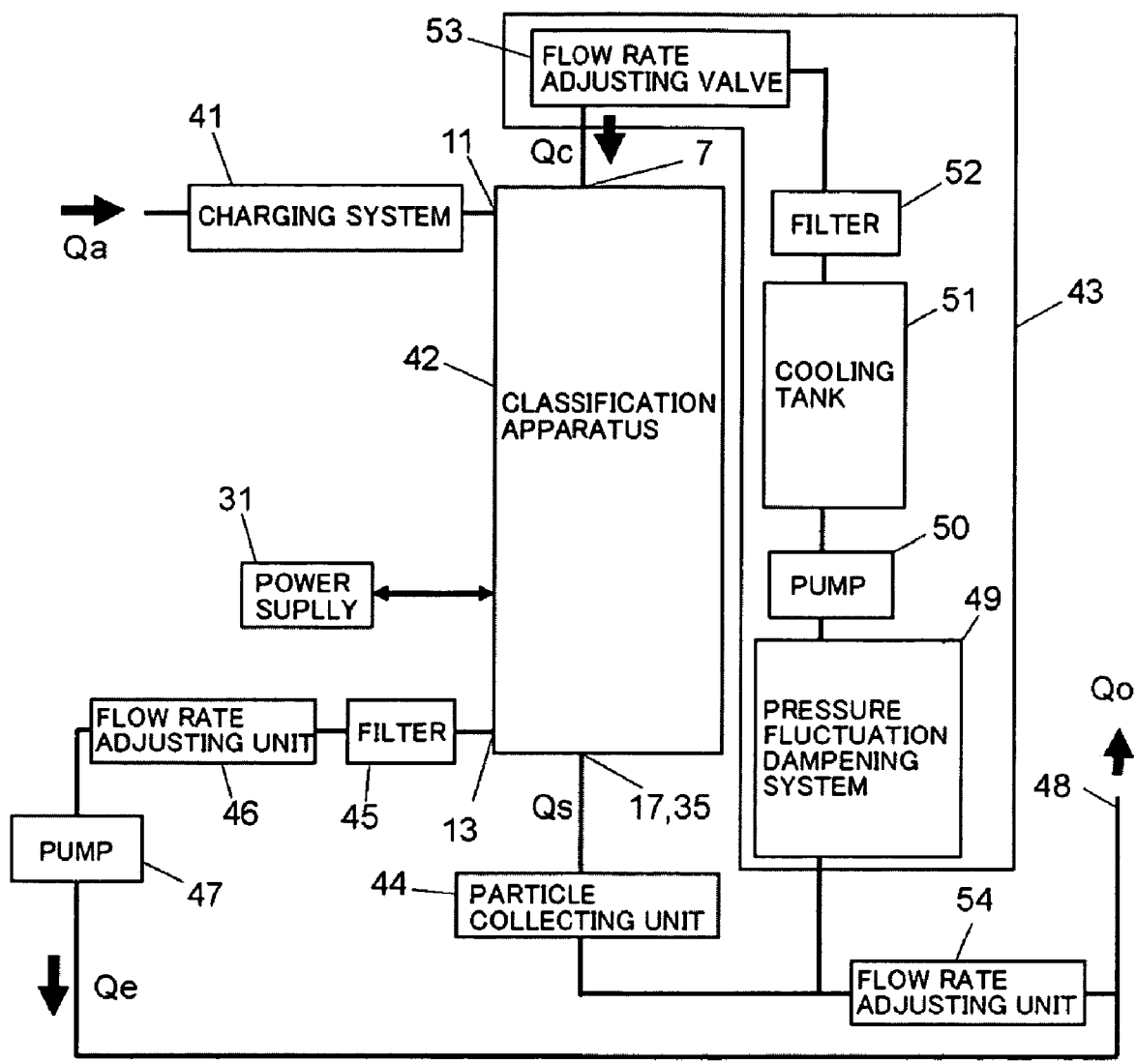

FIG. 10 is a schematic view of a particle collecting apparatus obtained by connecting a charging system, a gas supply system, and a particle collecting unit to the classification apparatus according to the present invention.

Figure 11:
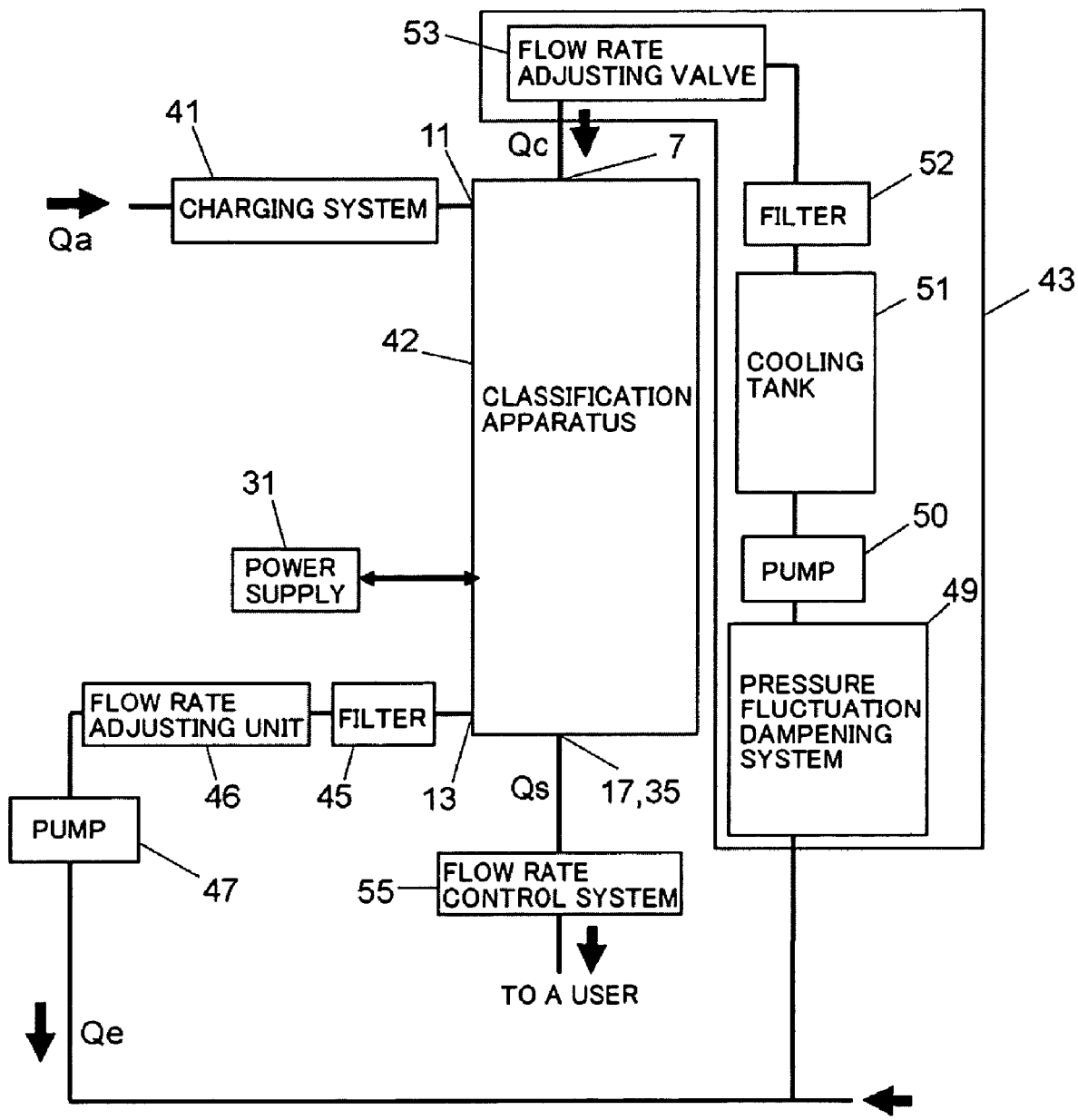

FIG. 11 is a schematic view of a particle separating apparatus obtained by connecting a charging system, a gas supply system, and a flow rate measuring system to the classification apparatus according to the present invention.

DESCRIPTION OF THE REFERENCE NUMERALS

1 housing
3 center electrode
4 outside electrode
5 classification region
7 sheath gas supply portion
9 flow straightener
11 aerosol supply portion
11a introduction port
12, 24 converging electrode
13 larger-size particle discharge portion
13a discharge port
14 smaller-size particle discharge portion
14a discharge port
16 outlet slit
17 sheath gas discharge portion
19 insulating member
21, 22, 23 pump
26 data processing unit
35 outlet
31 power supply
33 control unit

BEST MODES FOR CARRYING OUT THE INVENTION

Hereinbelow, the present invention will be described in detail based on the following embodiments.

Figure 1A:
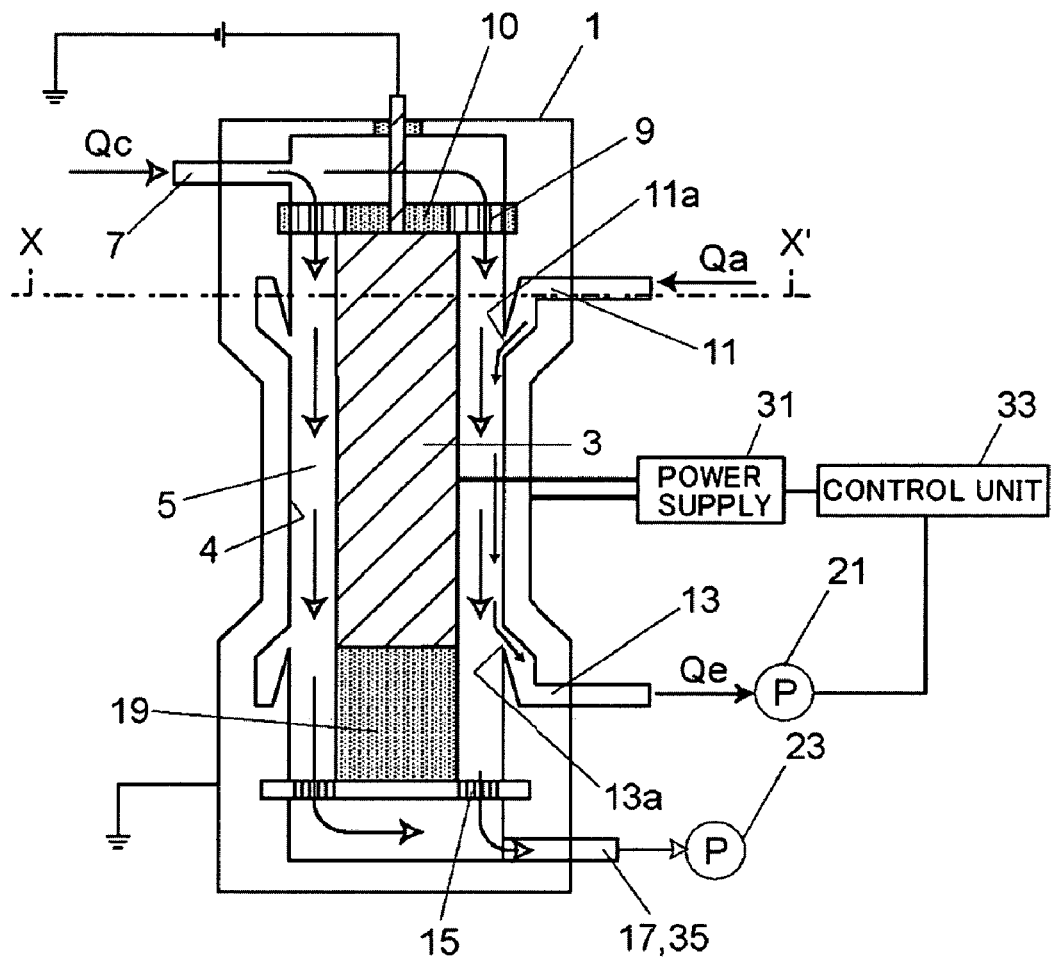
Figure 1B:
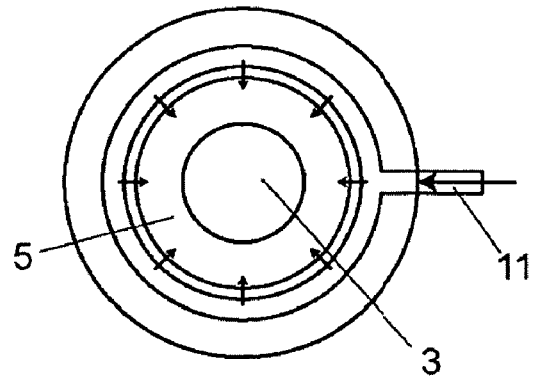

FIG. 1A is a vertical sectional view schematically showing a classification apparatus according to one embodiment of the present invention, and FIG. 1B is a horizontal sectional view taken along the X-X' line in FIG. 1A.

A cylindrical center electrode 3 is provided in a cylindrical housing 1 so that the central axis of the center electrode 3 is aligned with the central axis of the housing 1. The inner surface of the housing 1 provides an outside electrode 4. The center electrode 3 and the outside electrode 4 are opposed to each other. The center electrode 3 and the outside electrode 4 generate an electric field for classifying charged fine particles according to electric mobility. A space having the shape of a body of revolution is provided between the electrodes 3 and 4, and the space functions as a classification region 5. Both of the electrodes 3 and 4 are connected to a power supply 31, and the power supply 31 is connected to a control unit 33. The power supply 31 for applying a voltage across the electrodes 3 and 4 can be controlled by the control unit 33, and the power supply 31 and the control unit 33 constitute one example of a particle size selecting means.

In the upper part of the housing 1, a sheath gas supply portion 7 is provided to introduce a non-charged gas as a sheath gas at a constant flow rate. At the upper end of the classification region 5, a flow straightener 9 made of an insulating material is provided to laminarize the sheath gas flow, and therefore the sheath gas is supplied to the classification region 5 through the flow straightener 9.

On the outside electrode 4 side in the classification region 5, an introduction port 11a is provided. A charged aerosol is supplied through the introduction port 11a at a constant flow rate in a direction crossing the sheath gas flow. The introduction port 11a is connected to an aerosol supply portion 11.

A larger-size particle discharge portion 13 is provided to discharge charged fine particles, which are contained in the classified charged aerosol and have particle sizes larger than a predetermined particle size, together with part of the sheath gas. The larger-size particle discharge portion 13 has a discharge port 13a provided on the outside electrode 4 side in the classification region 5 and on the downstream side in the sheath gas flow. The flow rate of a gas discharged through the larger-size particle discharge portion 13 can be made constant.

In the lower part of the housing 1, that is, on the downstream side in the sheath gas flow, an outlet 35 (a sheath gas discharge portion 17) is provided outside the lower end of the classification region 5 to discharge remaining charged fine particles together with the sheath gas.

Pumps 21 and 23 are provided downstream of the larger-size particle discharge portion 13 and the outlet 35, respectively, as suction systems. The pump 21 is used to exhaust a gas from the inside of the housing 1 at a flow rate of 3.5 to 5.5 L/min, and the pump 23 is used to exhaust a gas from the inside of the housing 1 at a flow rate of 90 to 100 L/min. Each of the sheath gas supply portion 7 and the aerosol supply portion 11 has a flowmeter, and the flow rate of the sheath gas is set to about 100 L/min and the flow rate of the aerosol is set to 0.5 to 1.5 L/min.

The pump 21 is connected to the control unit 33. The pump 21 and the control unit 33 for controlling the pump 21 to adjust the flow rate of a gas discharged through the larger-size particle discharge portion 13 constitute one example of the particle size selecting means.

The upper end of the center electrode 3 is supported by the housing 1 by means of an insulating member 10 and the flow straightener 9 made of an insulating material, and the lower end of the center electrode 3 is supported by the housing 1 by means of an insulating member 19 and a supporting member 15 also serving as a flow straightener for laminarizing the sheath gas flow, and therefore the center electrode 3 is electrically insulated from the housing 1 providing the outside electrode 4.

The diameter of the center electrode 3 is 25 mm, and the inner diameter of the outside electrode 4 is 33 mm. The spacing between the center electrode 3 and the outside electrode 4 in the cylindrical part of the classification region 5 is kept constant to be about 4 mm. A voltage to be applied across the electrodes 3 and 4 for classification is 1000 to 1500 V.

Each of the introduction port 11a and the discharge port 13a has a width of 0.5 mm, and is formed along the inner circumferential surface of the outside electrode 4 to be shaped into a ring surrounding the center electrode 3. The distance between the introduction port 11a and the discharge port 13a is about 100 mm. It is to be noted that each of the introduction port 11a and the discharge port 13a may be shaped like a slit.

Hereinbelow, the operation of the classification apparatus according to this embodiment of the present invention will be described. First, a voltage is applied across the electrodes 3 and 4 so that an electric field for classifying charged fine particles according to electric mobility is generated in a horizontal direction in the classification region 5.

In this embodiment, when an aerosol is introduced into the classification region 5 through the introduction port 11a of the aerosol supply portion 11, charged fine particles having a particle size of, for example, about 20 nm reach near the center electrode 3 located on the opposite side of the classification region 5 and charged fine particles having particle sizes less than 20 nm are caught and removed by the center electrode 3. On the other hand, charged fine particles having particle sizes larger than 20 nm are distributed from near the center of the sheath gas flow to near the outside electrode 4 having the introduction port 11a.

As described above, the discharge port 13a is provided in the outside electrode 4, having the introduction port 11a, on the downstream side in the sheath gas flow. Charged fine particles having particle sizes larger than a certain particle size (e.g., 100 nm) are removed by discharging charged fine particles, contained in the charged aerosol and having particle sizes larger than a predetermined particle size, together with the sheath gas through the discharge port 13a by suction.

In this way, charged fine particles larger and smaller than a predetermined particle size range are removed, and then remaining charged fine particles are discharged through the outlet 35. The thus obtained fine particles can be used in etching processes in semiconductor production or for pharmaceutical products.

As described above, in order to achieve the removal of fine particles having particle sizes larger than a certain particle size, it is necessary to completely separate the distribution of charged fine particles having particle sizes around 100 nm from the distribution of charged fine particles having particle sizes around 130 nm in the sheath gas flow at a relatively low classification voltage which allows charged fine particles having a particle size of 20 nm to reach the opposite side of the classification region 5, and it is also necessary to remove only a gas flow, in which fine particles having particle sizes larger than 100 nm are distributed, through the discharge port 13a.

Therefore, an electric field for classification is first set so that the classification apparatus as DMA can have a high ability to classify fine particles according to electric mobility, and then the flow rate of a sheath gas (Qc), the flow rate of a charged aerosol gas (Qa), and the flow rate of a gas discharged through the larger-size particle discharge portion 13 (Qe) are adjusted. From the results of the following computational simulation of a fluid, it has been found that an appropriate ratio between the flow rate of a sheath gas and the flow rate of an aerosol gas is about 100:1. It is to be noted that this simulation was carried out using a software program FIDAP developed by Fluent.

Figure 2A:
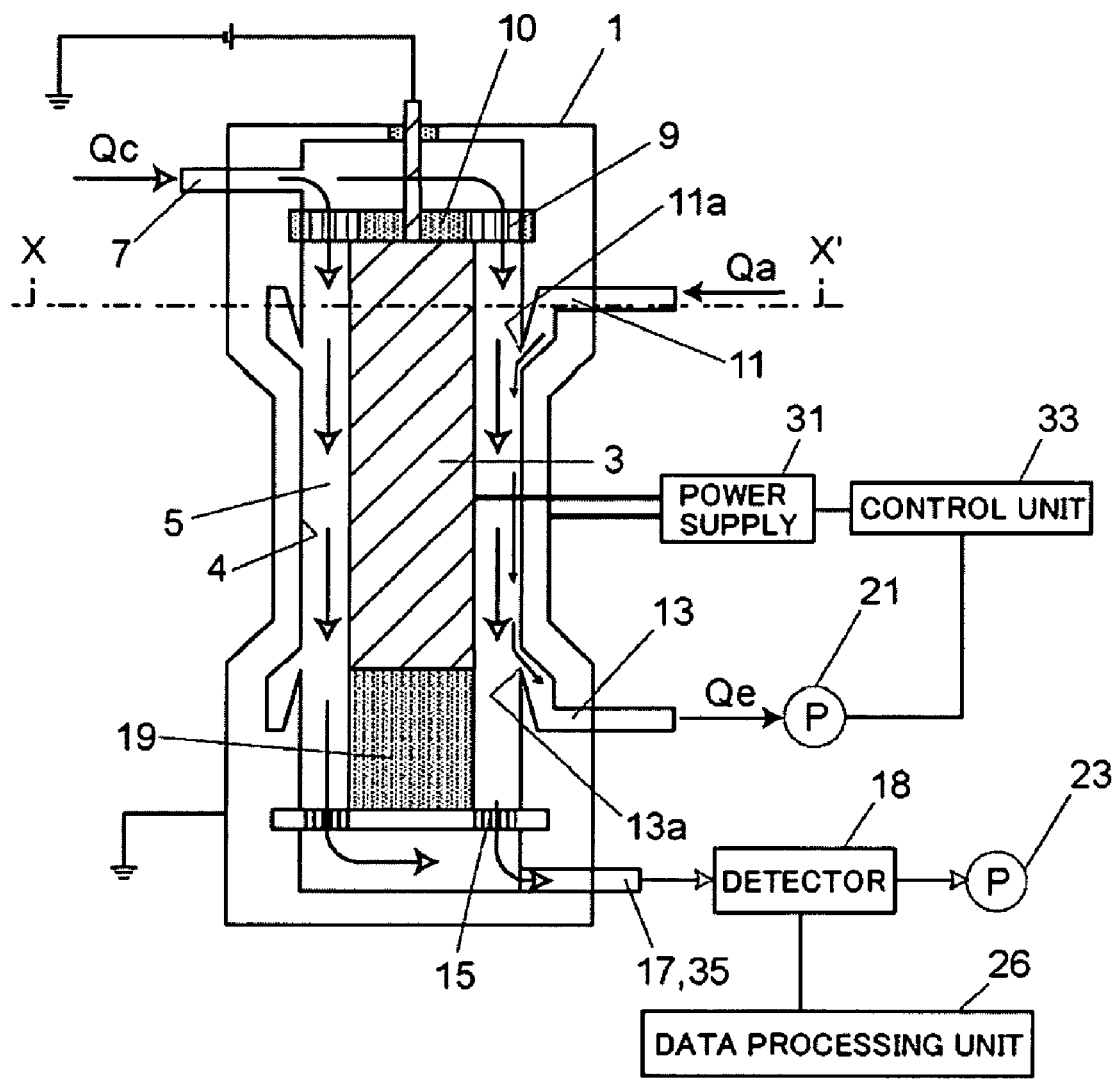
Figure 2B:
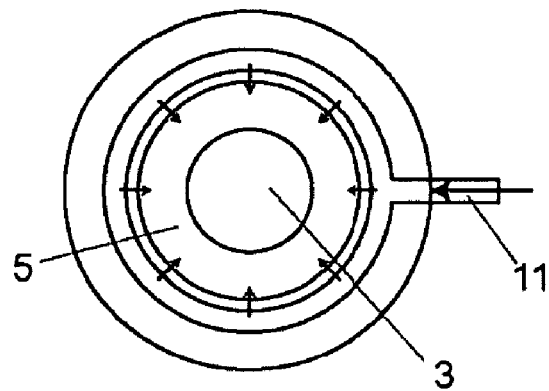
Figure 3A:
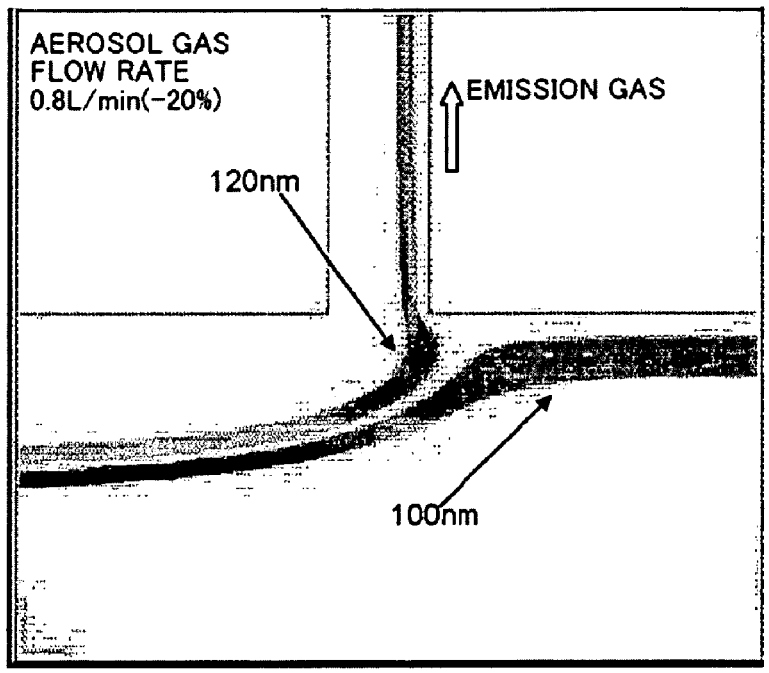
FIG. 3E is a simulation result showing the paths of charged fine particles having particle sizes of 100 nm and 120 nm, obtained by setting the flow rate of a sheath gas to 100 L/min, the flow rate of a gas discharged through the larger-size particle discharge portion 13 to 5.0 L/min, and the flow rate of an aerosol gas to 1.2 L/min.
Figure 3B:
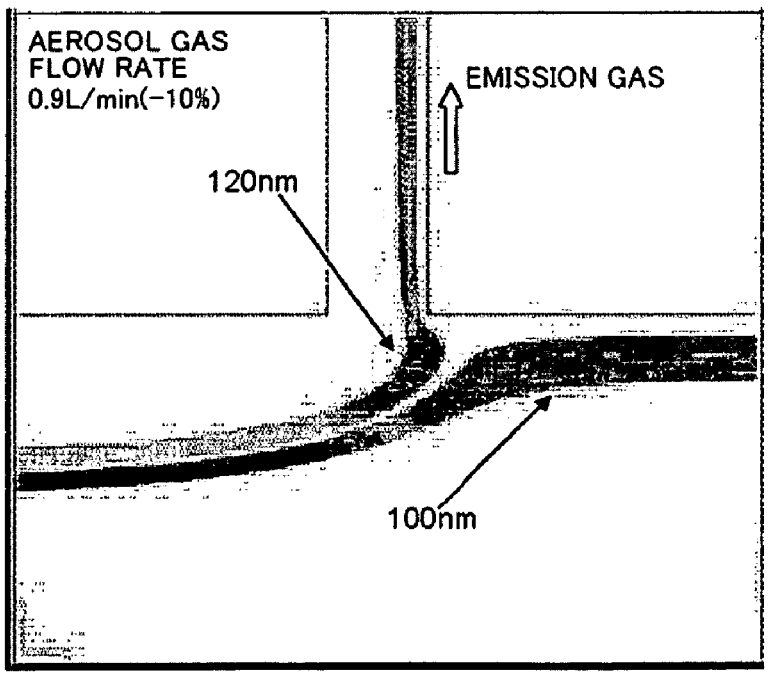
Figure 3C:
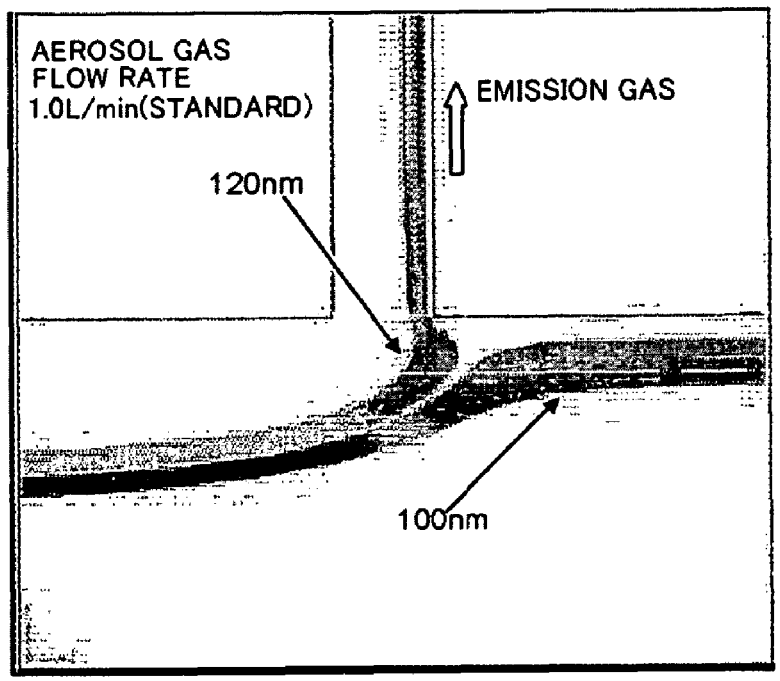
Figure 3D:
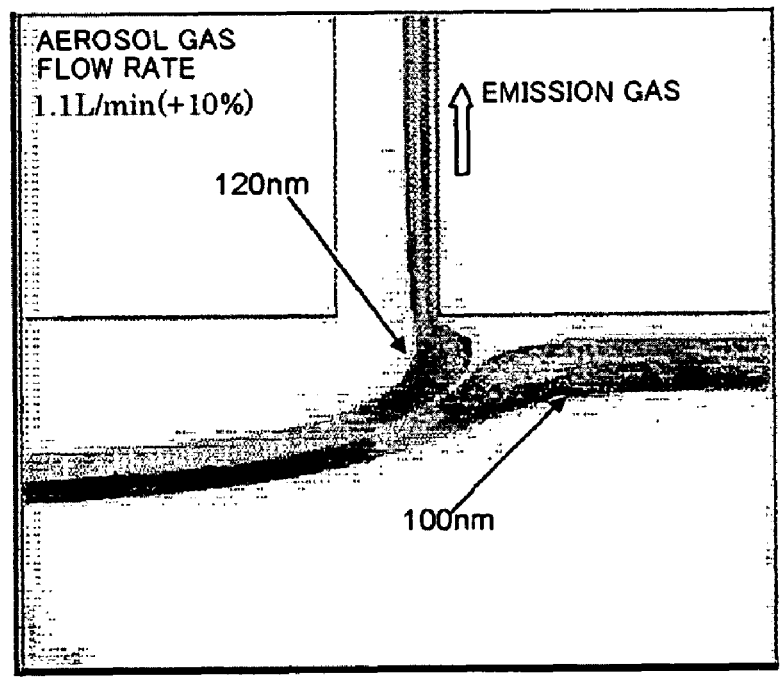
Figure 3E:
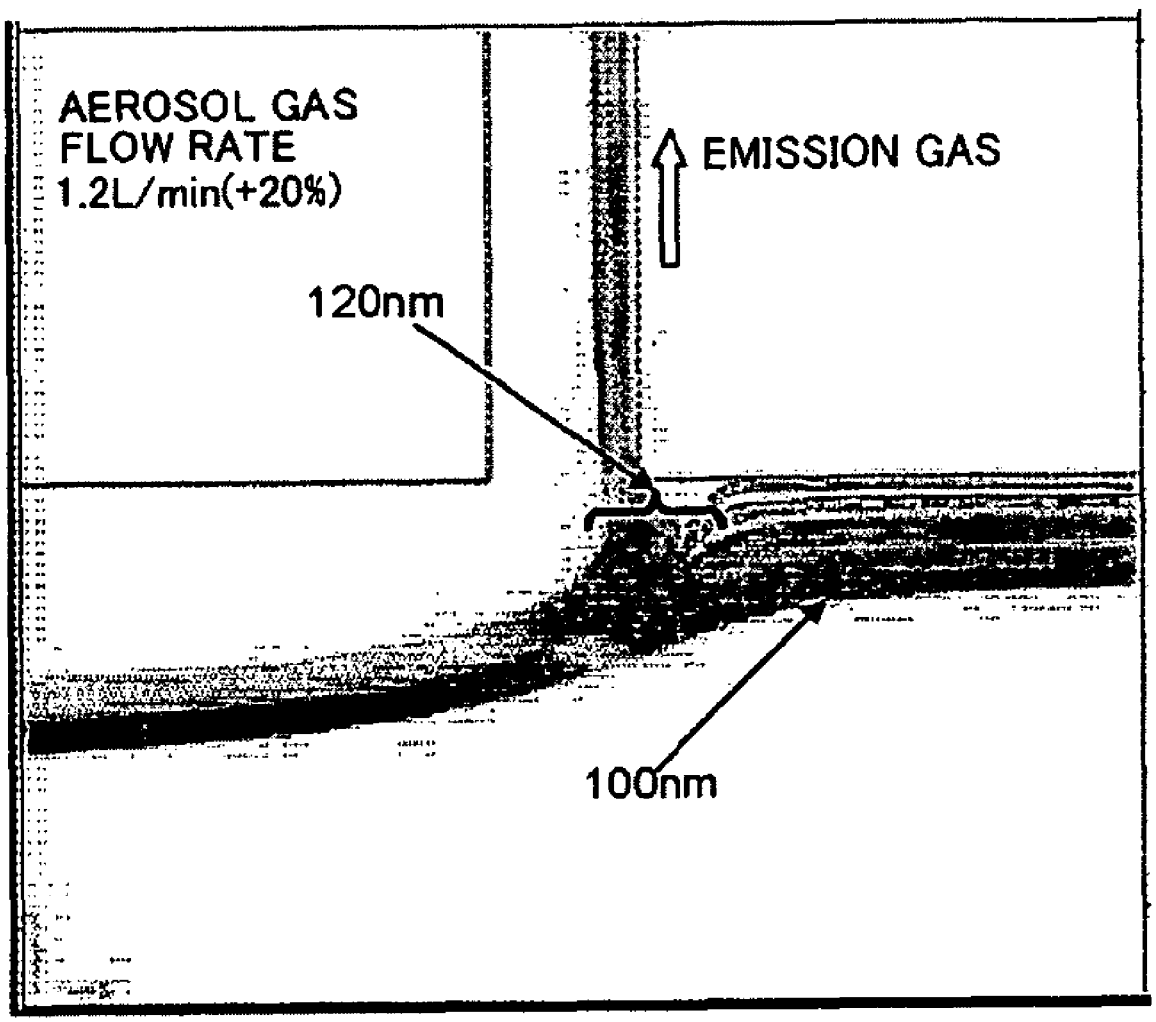

The structure of a fine particle measuring apparatus for measuring particle distribution is shown in FIG. 2.

The fine particle measuring apparatus includes the classification apparatus shown in FIG. 1 and a detector 18 provided downstream of the outlet 35 (sheath gas discharge portion 17). The detector 18 detects the number of remaining charged fine particles contained in a sheath gas introduced thereinto as the quantity of electricity.

The pumps 21 and 23 are provided downstream of the larger-size particle discharge portion 13 and the detector 18, respectively, as suction systems. The pump 21 is used to exhaust a gas from the inside of the housing 1 at a flow rate of 3.5 to 5.5 L/min, and the pump 23 is used to exhaust a gas from the inside of the housing 1 at a flow rate of 90 to 100 L/min. Each of the sheath gas supply portion 7 and the aerosol supply portion 11 has a flowmeter. The flow rate of a sheath gas was set to about 100 L/min, and the flow rate of an aerosol was set to 0.5 to 1.5 L/min.

FIGS. 3 to 6 show the results of the simulation. In order to satisfy sensitivity conditions required of the simulation, the flow rate of an aerosol gas was set to a value in the range of 0.8 to 1.2 L/min and the flow rate of a sheath gas was set to a value in the range of 96 to 104 L/min, and the paths of particles having particle sizes of 20, 21, 22, 100, 120, and 150 nm were simulated by changing the flow rate of a sheath gas or the flow rate of an aerosol gas within the above range.

A general DMA uses a Faraday cup electrometer as a detector, and an object to be measured by the detector is a gas having a flow rate of about 3 L/min or less. Therefore, when a sheath gas supplied at a flow rate of about 100 L/min needs to be entirely passed through the detector, a fine-particle collector designed to be capable of treating a gas having a flow rate of 100 L/min is selected for the detector.

FIGS. 3A to 3E show the paths of charged fine particles, having particle sizes of 100 nm and 120 nm, obtained by changing the flow rate of an aerosol gas (Qa) around 1 L/min while keeping the flow rate of a sheath gas (Qc) at 100 L/min and keeping the flow rate of a gas discharged through the larger-size particle discharge portion 13 (Qe) at 5.0 L/min. In FIGS. 3A to 3E, the flow rates of an aerosol gas are 0.8 L/min (−20% relative to 1 L/min), 0.9 L/min (−10% relative to 1 L/min), 1.0 L/min, 1.1 L/min (+10% relative to 1.0 L/min), and 1.2 L/min (+20% relative to 1.0 L/min), respectively.

As can be seen from FIGS. 3A to 3E, a reduction in the flow rate of an aerosol gas does not impair the ability of the classification apparatus to classify (separate) fine particles according to electric mobility. However, in a case where the flow rate of an aerosol gas is increased to 1.2 L/min, the classification apparatus cannot completely separate charged fine particles having a particle size of 100 nm and charged fine particles having a particle size of 120 nm from each other any longer, it follows that the flow rate of an aerosol gas has a significant effect on the ability of the classification apparatus to separate fine particles according to electric mobility. On the other hand, a region, in which fine particles having a small particle size such as 20 nm are distributed, is not significantly affected by such a level of change in the flow rate of an aerosol gas.

Figure 4A:
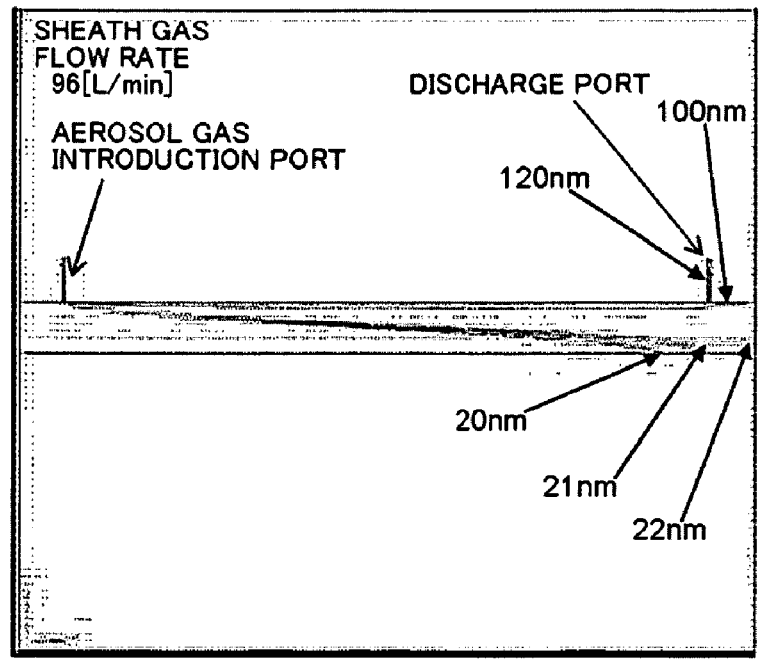
FIG. 4A is a simulation result showing the paths of charged fine particles having particle sizes of 20, 21, 22, 100, and 120 nm, obtained by setting the flow rate of an aerosol gas to 1.0 L/min, the flow rate of a gas discharged through the larger-size particle discharge portion 13 to 5.0 L/min, and the flow rate of a sheath gas to 96 L/min.
Figure 4B:
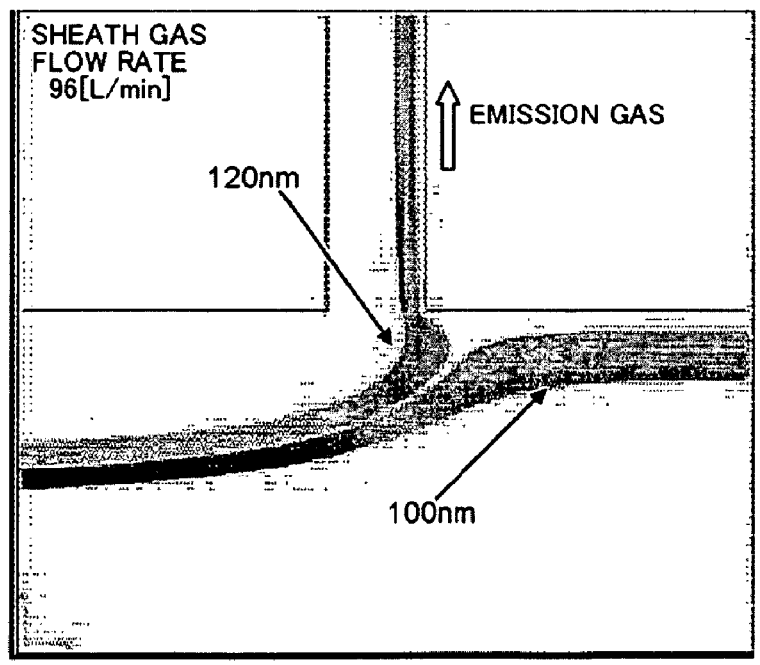
FIG. 4B is a view showing the paths of charged fine particles near a discharge port shown in FIG. 4A.
Figure 4E:
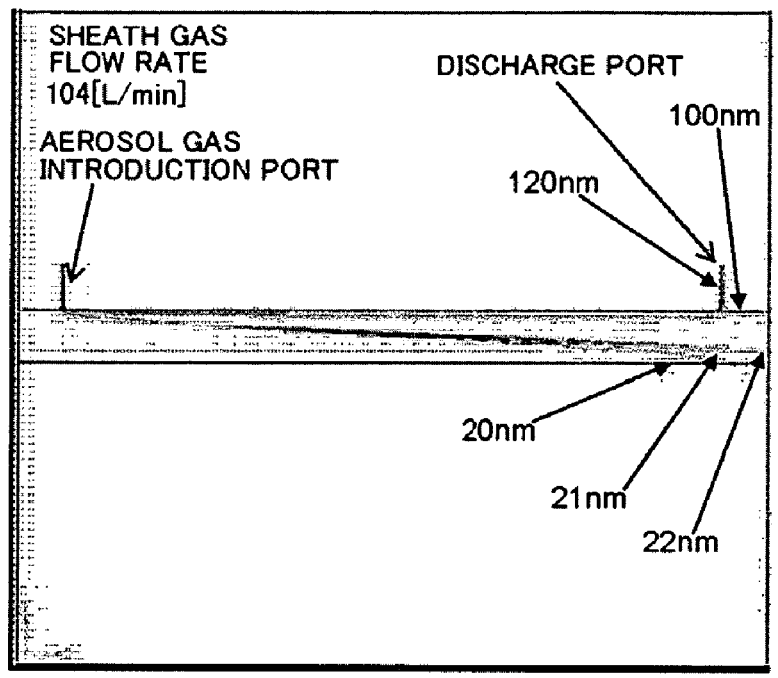
FIG. 4E is a simulation result showing the paths of charged fine particles having particle sizes of 20, 21, 22, 100, and 120 nm, obtained by setting the flow rate of an aerosol gas to 1.0 L/min, the flow rate of a gas discharged through the larger-size particle discharge portion 13 to 5.0 L/min, and the flow rate of a sheath gas to 104 L/min.
Figure 4F:
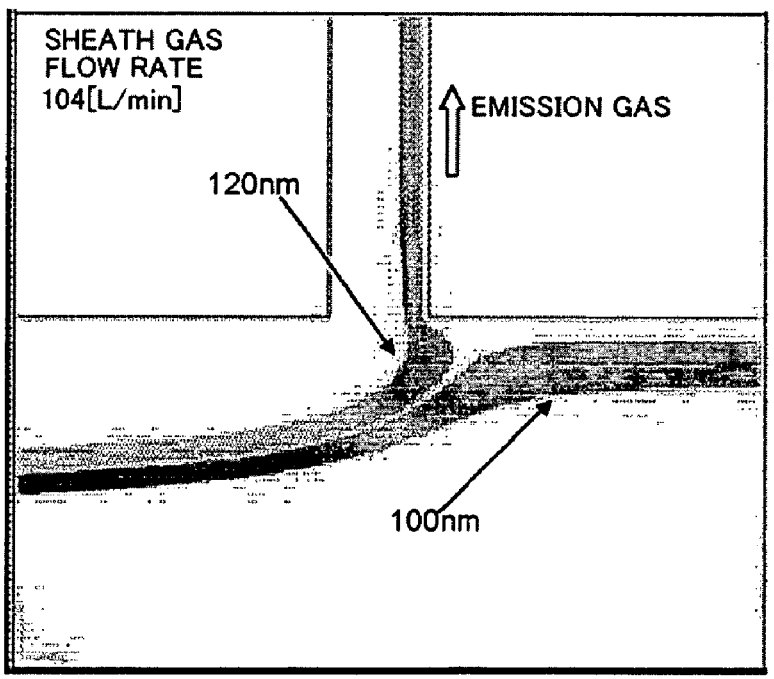
FIG. 4F is an enlarged view showing the paths of charged fine particles near a discharge port shown in FIG. 4E.

FIGS. 4A to 4F show the paths of charged fine particles, having particle sizes of 20, 21, 22, 100, and 120 nm, obtained by changing the flow rate of a sheath gas around 100 L/min while keeping the flow rate of an aerosol gas at 1.0 L/min and keeping the flow rate of a gas discharged through the larger-size particle discharge portion 13 at 5.0 L/min. In FIGS. 4A, 4C, and 4E, the flow rates of a sheath gas are 96 L/min (−4% relative to 100 L/min), 100 L/min, and 104 L/min (+4% relative to 100 L/min), respectively. FIGS. 4B, 4D, and 4F are enlarged views showing the paths of fine particles near the discharge port of the larger-size particle discharge portion 13 shown in FIGS. 4A, 4C, and 4E, respectively.

From the results shown in FIGS. 4A to 4F, it has been found that even when the flow rate of a sheath gas is changed by about ±4% relative to 100 L/min, the ability of the classification apparatus to classify fine particles according to electric mobility is not so significantly affected.

Figure 5:
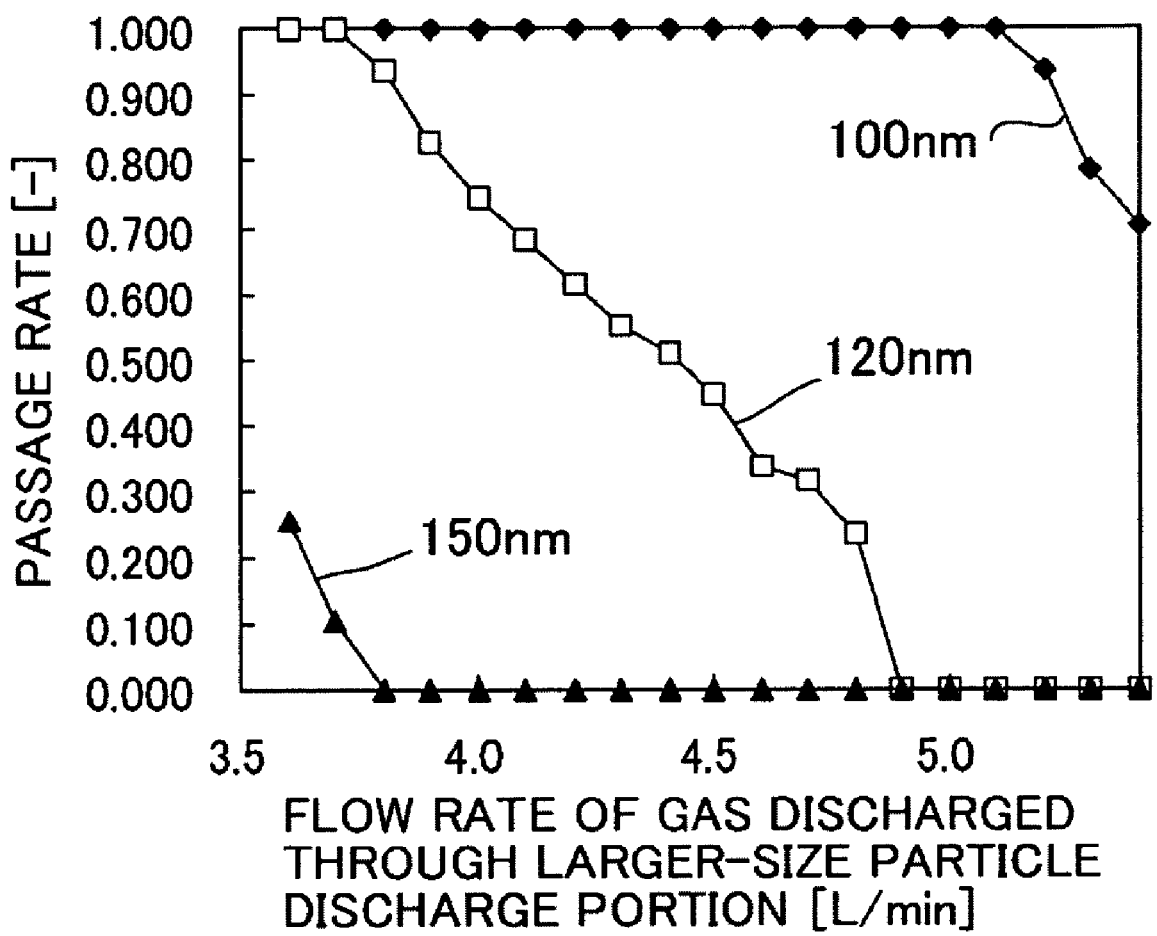
FIG. 5 is a graph showing a change in passage rate when the flow rate of a gas discharged through the larger-size particle discharge portion is changed while the flow rate of a sheath gas is kept at 100 L/min and the flow rate of an aerosol gas is kept at 1.0 L/min.

FIG. 5 is a graph showing a change in passage rate caused by changing the flow rate of a gas discharged by the pump 21 connected to the larger-size particle discharge portion 13 while keeping the flow rate of a sheath gas at 100 L/min and keeping the flow rate of an aerosol gas at 1.0 L/min. It is to be noted that the term "passage rate" means the rate of fine particles that reach the detector without being discharged through the larger-size particle discharge portion 13, and a passage rate of 1.0 means that fine particles are not discharged through the larger-size particle discharge portion 13 at all, and a passage rate of 0 means that fine particles are all discharged through the larger-size particle discharge portion 13. In FIG. 5, the horizontal axis represents the flow rate of a gas discharged through the larger-size particle discharge portion 13 (L/min), and the vertical axis represents the passage rate.

As can be seen from FIG. 5, when the flow rate of a gas discharged through the larger-size particle discharge portion 13 is in the range of 4.9 to 5.1 L/min, it is possible to separate charged fine particles having a particle size of 100 nm and charged fine particles having a particle size of 120 nm from each other, and when the flow rate of a gas discharged through the larger-size particle discharge portion 13 is in the range of 3.8 to 5.1 L/min, it is possible to separate charged fine particles having a particle size of 100 nm and charged fine particles having a particle size of 150 nm from each other.

Figure 6A:
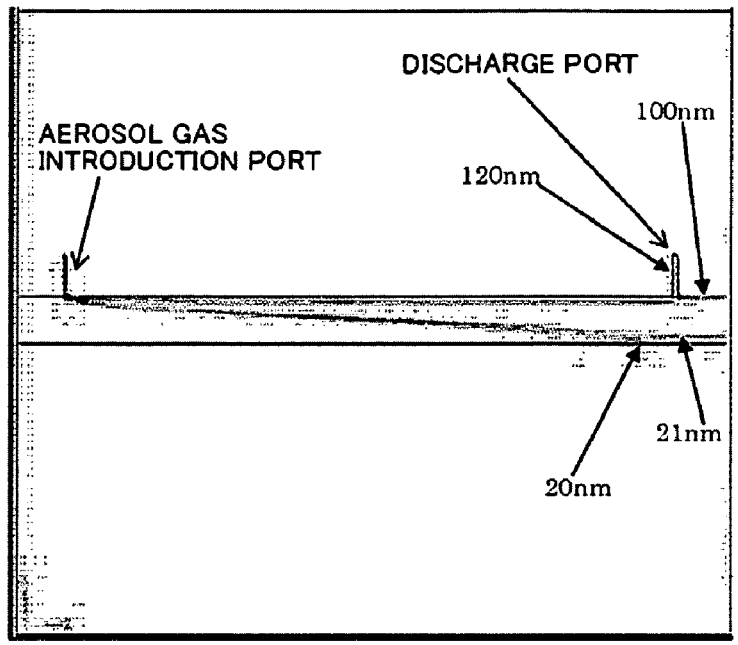
FIG. 6A is a simulation result showing the paths of charged fine particles having particle sizes of 20, 21, 100, and 120 nm, obtained by setting the flow rate of a sheath gas to 100 L/min, the flow rate of an aerosol gas to 1.0 L/min, and the flow rate of a gas discharged through the larger-size particle discharge portion to 5.0 L/min.
Figure 6B:
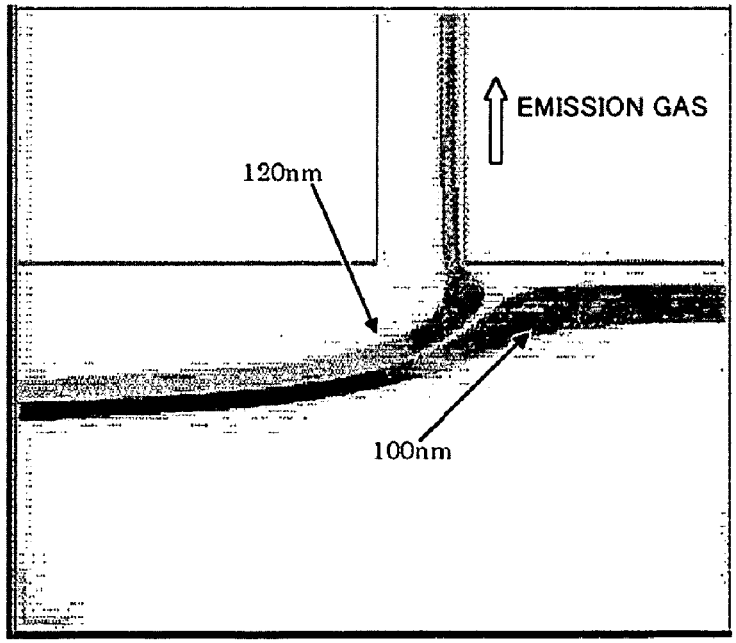
FIG. 6B is a view showing the paths of charged fine particles near a discharge port shown in FIG. 6A.

FIGS. 6A and 6B show the paths of charged fine particles simulated at the flow rate of a gas discharged through the larger-size particle discharge portion 13 of 5 L/min under basic conditions (flow rate of sheath gas: 100 L/min, flow rate of aerosol gas: 1.0 L/min). More specifically, FIG. 6A shows the paths of charged fine particles having particle sizes of 20, 21, 100, and 120 nm, and FIG. 6B is an enlarged view of an area in the vicinity of the discharge port 13a shown in FIG. 6A. From the simulation result shown in FIGS. 6A and 6B, it has been found that by setting the flow rate of a gas discharged through the larger-size particle discharge portion 13 to 5 L/min, it is possible to separate charged fine particles having a particle size of 100 nm and charged fine particles having a particle size of 120 nm from each other.

From the above simulation results, it has been found that by adjusting the flow rate of a sheath gas (Qc), the flow rate of an aerosol gas (Qa), and the flow rate of a gas discharged through the larger-size particle discharge portion 13 (Qe) as parameters, it is possible to selectively measure fine particles having particle sizes within a desired range. The fine particle measuring apparatus according to the present invention can measure fine particles having particle sizes within a desired range by setting an electric field to be applied to the classification region 5 and adjusting these parameters, and the classification apparatus according to the present invention can separate fine particles having particle sizes within such a desired range.

Hereinbelow, the relationship between operational conditions and characteristics (passage rate characteristics) of fine particles discharged through the outlet 35 (sheath gas discharge portion 17) will be described based on results obtained by changing as operational parameters, the flow rate of a sheath gas (Qc), the flow rate of a gas discharged through the larger-size particle discharge portion (Qe) and a voltage V to be applied to the classification region.

In FIG. 7, the vertical axis represents the ratio (passage rate) of fine particles discharged through the outlet 35 to fine particles contained in an aerosol supplied from the aerosol supply portion 11, and the horizontal axis represents the particle sizes (nm) of fine particles discharged through the outlet 35. In a case where the passage rate of fine particles having a certain particle size is 0, it means that almost 100% of the fine particles are removed.

In the legends on the right side of the graph, "Qc" and "Qe" in the explanation of each symbol represent the flow rate of a sheath gas (sLm: standard L/m) and the flow rate of a gas discharged through the discharge port 13a (sLm), respectively, and numbers in parentheses are classification voltages. The flow rate of a sheath gas (Qc) was kept at 60 sLm.

As can be seen from the graph shown in FIG. 7, when Qe is kept constant, fine particles having relatively small particle sizes are more likely to be removed by increasing the classification voltage. On the other hand, when the classification voltage is kept constant, fine particles having relatively large particle sizes are more likely to be removed by increasing Qe. From the results, it has been found that a trapezoidal transfer function can be achieved.

Further, from the results, it has also been found that the particle size range of particles to be detected can easily be changed by changing the operational conditions and that not only accumulation mode particles but also only nuclei mode particles can be collected.

Referring to FIG. 2 again, the detector 18 is connected to a data processing unit 26. The data processing unit 26 retains the previously-determined charging rate of an aerosol as a measuring object such as car exhaust, and calculates the fine particle number concentration of the measured aerosol based on the quantity of electricity measured by the detector 18. By providing the data processing unit 26 in the fine particle measuring apparatus, it is possible to automatically determine the particle number concentration of a measured aerosol online.

It is to be noted that a fine particle measuring apparatus according to other embodiments of the present invention, which will be described later, may also have such a data processing unit 26.

FIG. 8A is a vertical sectional view schematically showing a fine particle measuring apparatus having a smaller-size particle discharge portion according to another embodiment of the present invention; FIG. 8B is a horizontal sectional view taken along the X-X' line in FIG. 8A; and FIG. 8C is a schematic view showing a particle size distribution in an area surrounded by a broken line in FIG. 8B.

A housing 1 and a center electrode 3 provided in the housing 1 have the same structures as those of the classification apparatus shown in FIGS. 1 and 2. The fine particle measuring apparatus shown in FIG. 8 further includes a smaller-size particle discharge portion 14 to discharge charged fine particles, which are contained in a classified charged aerosol and have particle sizes smaller than a predetermined particle size, together with part of a sheath gas at a constant flow rate. The smaller-size particle discharge portion 14 has a discharge port 14a provided on the center electrode 3 side in a classification region 5 and on the downstream side in the sheath gas flow. A pump 22 as a discharge system is further provided downstream of the smaller-size particle discharge portion 14 to discharge charged fine particles together with the sheath gas. The pump 22 exhausts a gas from the classification region 5 at a constant flow rate. It is to be noted that the smaller-size particle discharge portion 14, the pump 22 for adjusting the flow rate of a gas discharged through the smaller-size particle discharge portion 14 and a control unit 33 for controlling the pump 22 constitute one example of the particle size selecting means.

The flow rate of a gas discharged through the smaller-size particle discharge portion 14 is set so that charged fine particles having particle sizes smaller than a predetermined particle size, for example, smaller than 20 nm can be reliably discharged. As described above, classified charged fine particles having particle sizes smaller than a predetermined range can be removed by allowing the center electrode 3 to adsorb them, but by providing the smaller-size particle discharge portion 14, it is possible to more reliably remove fine particles having particle sizes smaller than a predetermined range.

In a case where the smaller-size particle discharge portion 14 is provided to remove fine particles having particle sizes smaller than a predetermined range, the above-described method for removing fine particles having particle sizes smaller than a predetermined range by allowing the electrode to adsorb them may be used together, or one of the methods may be used singly. It is to be noted that by using these methods together, it is possible to more reliably remove fine particles having particle sizes smaller than a predetermined range.

The fine particle measuring apparatus shown in FIG. 8 includes a detector 18 provided downstream of a sheath gas discharge portion 17 (an outlet 35), but may be used as a classification apparatus as shown in FIG. 1 by omitting the detector 18 to obtain fine particles having particle sizes within a predetermined particle size distribution range.

FIG. 9A is a vertical sectional view schematically showing a fine particle measuring apparatus having converging electrodes according to another embodiment of the present invention, and FIG. 9B is a horizontal sectional view taken along the X-X' line in FIG. 9A.

A housing 1 and a center electrode 3 provided in the housing 1 have the same structures as those of the classification apparatus shown in FIG. 1. As described above, the fine particle measuring apparatus shown in FIG. 9 includes converging electrodes 12 and 24 in an area between a classification region 5 and a detector 18. The converging electrodes 12 and 24 are opposed to each other to generate an electric field opposite in direction to that generated by the electrodes 3 and 4 for forming a classification region to converge classified charged fine particles. The converging electrode 12 is an outside electrode united with the electrode 4, and has the same potential as the electrode 4. In this embodiment, both the converging electrode 12 and the electrode 4 are at ground potential. Like the electrode 3, the converging electrode 24 is a center electrode, but an insulating member 19 is provided under the electrode 3 so as to be interposed between the electrode 3 and the converging electrode 24. A direct voltage is applied to the electrode 3 and the converging electrode 24 through a concentric cable 25, and the electrode 3 and the converging electrode 24 have opposite electric potentials.

Further, an outlet slit 16 is provided between the converging electrodes 12 and 24 and the detector 18 to selectively discharge converged charged fine particles together with part of a sheath gas. By providing the outlet slit 16, it is possible to discharge only charged fine particles converged by the converging electrodes 12 and 24 through the outlet 35 or to prevent part of a sheath gas not containing charged fine particles from being introduced into the detector 18 when charged fine particles, converged by the converging electrodes 12 and 24 and discharged through the outlet 35, are introduced into the detector 18. The outlet slit 16 has a size allowing charged fine particles converged by the converging electrodes 12 and 24 to pass through, and is provided on the inner circumferential surface side of the outside electrode 12 so as to be shaped into a ring surrounding the center electrode 24.

Also in the fine particle measuring apparatus shown in FIG. 9, the electrodes 3 and 24 are preferably supported by the housing 1 by means of an insulating member 20 provided at the lower end of the center electrode 24.

As described above, by providing the converging electrodes 12 and 24, it is possible to converge classified charged fine particles. Therefore, even when the outlet slit 16 is not provided, the size of the detector 18 can be reduced because only the charged fine particles converged by the converging electrodes are detected by the detector 18.

In a case where the outlet slit 16 is also provided, the flow rate of a sheath gas introduced into the detector 18 can be reduced and therefore the size of the detector 18 can be further reduced.

The fine particle measuring apparatus shown in FIG. 9 includes the detector 18 provided downstream of the outlet 35, but may be used as a classification apparatus as shown in FIG. 1 by omitting the detector 18.

By providing converging electrodes in the classification apparatus, it is possible to prevent charged fine particles from being attached to the wall surface of the classification apparatus, and therefore, to accurately collect charged fine particles from the outlet.

In recent years, some researchers have been concerned about the effect of nuclei mode particles on health. In this regard, the present inventors have demonstrated that the classification apparatus and fine particle measuring apparatus according to the present invention can be effectively used as a means for measuring such nuclei mode particles. These apparatuses according to the present invention can also be used for various purposes other than measurement in industrial fields. For example, the classification apparatus according to the present invention can be used as an apparatus for collecting classified fine particles in production of pharmaceutical products such as missile drugs or for surface polishing in semiconductor production processes.

For example, it is known that a nanometer-sized drug does not induce an immune reaction because of its small size and is easily absorbed by cells, and therefore it is to be expected that a nanometer-sized drug having target directivity will be used as a missile drug which can selectively act on an affected area. Further, it has been reported based on research results that nanometer-sized abrasive particles having a uniform particle size are suitable for surface polishing of silicon wafers used in semiconductor industry.

Hereinbelow, application examples utilizing the classification apparatus according to the present invention will be described with reference to FIGS. 10 and 11.

FIG. 10 is a schematic view of a particle collecting apparatus obtained by connecting a charging system, a gas supply system and a particle collecting unit to the classification apparatus according to the present invention.

As shown in FIG. 10, the particle collecting apparatus includes a charging system 41 for electrically charging an aerosol, a classification apparatus 42 for classifying charged particles contained in a charged aerosol according to electric mobility, a particle collecting unit 44 for collecting classified particles discharged from the classification apparatus 42, and a sheath gas supply system 43 for supplying a sheath gas. The charging system 41, the particle collecting unit 44, and the sheath gas supply system 43 are connected to the classification apparatus 42. The classification apparatus 42 has a pair of electrodes opposed to each other, and these electrodes are connected to a power supply 31.

In the upper part of the classification apparatus 42, a sheath gas supply portion 7 is provided. The sheath gas supply portion 7 is connected to the sheath gas supply system 43, and a non-charged sheath gas is supplied to the classification apparatus 42 at a flow rate Qc.

The classification apparatus 42 is connected to the charging system 41 through an aerosol supply portion 11, and an aerosol charged by the charging system 41 is supplied to the classification apparatus 42 at a sample gas flow rate Qa.

On the downstream side in the classification apparatus 42, a larger-size particle discharge portion 13 for discharging a gas to the outside of a classification region at a flow rate Qe is provided.

Further, a filter 45 for removing fine particles, a flow rate adjusting unit 46 for measuring and adjusting the gas flow rate Qe and a pump 47 are provided downstream of the larger-size particle discharge portion 13. A gas flowing through the filter 45, the flow rate adjusting unit 46 and the pump 47 is discharged through a gas discharge portion 48 at a flow rate Qo.

The classification apparatus 42 is connected to the particle collecting unit 44 through a sheath gas discharge portion 17 (an outlet 35). A sheath gas containing fine particles having particle sizes within a predetermined range is discharged through the sheath gas discharge portion 17 at a flow rate Qs. The particle collecting unit 44 is connected through a flow rate adjusting unit 54 to the gas discharge portion 48 provided downstream of the particle collecting unit 44.

The sheath gas supply system 43 includes a flow path connected between the particle collecting unit 44 provided upstream of the sheath gas supply system 43 and the sheath gas supply portion 7 provided downstream of the sheath gas supply system 43, a pump and the like. More specifically, a pressure fluctuation dampening system 49 is provided downstream of the particle collecting unit 44, and a pump 50 for delivering a sheath gas, a cooling tank 51 for keeping a sheath gas at around room temperature, a filter 52 for removing fine particles from a sheath gas and a flow rate adjusting valve 53 for adjusting the flow rate of a sheath gas are provided downstream of the pressure fluctuation dampening system 49 in this order.

In the particle collecting apparatus shown in FIG. 10, since particles are electrically charged, the particle collecting unit 44 may use an electrostatic scrubber to collect charged particles in batches. Alternatively, in a case where particles to be collected are heat-resistant particles such as titania particles, these particles may be collected by a filter such as a cotton filter. In this case, particles can be obtained by burning the filter. By using such a method, it is possible to collect and analyze fine particles having a predetermined particle size.

FIG. 11 is a schematic view of a particle selecting apparatus obtained by connecting a charging system, a gas supply system and a flow rate measuring system to the classification apparatus according to the present invention.

As shown in FIG. 11, the particle selecting apparatus includes a charging system 41 for electrically charging an aerosol, a classification apparatus 42 for classifying charged particles contained in a charged aerosol according to electric mobility, a flow rate control system 55 for adjusting the flow rate of classified particles discharged from the classification apparatus 42 and transferring these particles to a place where they are used, and a sheath gas supply system 43. The charging system 41, the flow rate control system 55, and the sheath gas supply system 43 are connected to the classification apparatus 42.

As in the case of the particle collecting apparatus shown in FIG. 10, in the upper part of the classification apparatus 42, a sheath gas supply portion 7 is provided, and the sheath gas supply portion 7 is connected to the sheath gas supply system 43 to supply a non-charged sheath gas to the classification apparatus 42 at a flow rate Qc. The classification apparatus 42 is connected to the charging system 41 through an aerosol supply portion 11 to supply an aerosol charged by the charging system 41 to the classification apparatus 42 at a sample gas flow rate Qa. The classification apparatus 42 has a pair of electrodes opposed to each other, and these electrodes are connected to a power supply 31.

On the downstream side in the classification apparatus 42, a larger-size particle discharge portion 13 is provided to discharge a gas to the outside of a classification region at a flow rate Qe.

Further, a filter 45 for removing fine particles, a flow rate adjusting unit 46 for measuring and adjusting the gas flow rate Qe and a pump 47 are provided downstream of the larger-size particle discharge portion 13. A gas flowing through the filter 45, the flow rate adjusting system 46 and the pump 47 is sent to the sheath gas supply system 43 and then reused as a sheath gas. A shortfall in sheath gas supply can be made up by feeding a fresh sheath gas from an outside source.

From the flow rate control system 55 provided downstream of the classification apparatus 42, a gas containing particles having a predetermined particle size is discharged, and then the gas is transferred to a place where it is used by a user.

In the case of the particle selecting apparatus shown in FIG. 11, air containing classified particles having particle sizes within a desired range is transferred to a place where a user wants to use it.

INDUSTRIAL APPLICABILITY

The present invention can be applied to a classification apparatus for separating fine particles, having particle sizes within a predetermined range, from environmental gas and an apparatus for measuring the number of fine particles separated by the classification apparatus.

The invention claimed is:

1. A classification apparatus comprising:
   a pair of electrodes including a first and a second electrodes opposed to each other to generate an electric field for classifying charged fine particles according to electric mobility to form a classification region, the first electrode attracting the charged fine particles;
   a sheath gas supply portion for supplying a non-charged gas as a sheath gas to the classification region from one end of the classification region;
   an aerosol supply portion having an introduction port provided on the second electrode side and on the upstream side in the sheath gas flow for supplying a charged aerosol through the introduction port;
   a larger-size particle discharge portion having a discharge port provided on the second electrode side and on the downstream side in the sheath gas flow for discharging charged fine particles having particle sizes larger than a predetermined particle size among the classified charged fine particles in the charged aerosol together with part of the sheath gas; and
   an outlet provided on the other end side of the classification region and downstream of the larger-size particle discharge portion in the sheath gas flow for discharging remaining charged fine particles together with the sheath gas, thereby removing the remaining charged fine particles having particle sizes smaller than the particle sizes of the particles removed by the larger-size particle discharge portion.

2. The classification apparatus according to claim 1, wherein the larger-size particle discharge portion discharges the charged fine particles together with part of the sheath gas at a constant flow rate.

3. The classification apparatus according to claim 1, further comprising particle size selecting means whereby the particle distribution range of the charged fine particles to be discharged through the outlet is adjusted.

4. The classification apparatus according to claim 3, wherein the particle size selecting means adjusts the particle distribution range by controlling the flow rate of a gas discharged through the larger-size particle discharge portion and/or a voltage applied between the electrodes opposed to each other.

5. The classification apparatus according to claim 4, wherein the particle size selecting means controls the flow rate of a pump connected downstream of the larger-size particle discharge portion to discharge charged fine particles having particle sizes larger than a predetermined particle size together with part of the sheath gas.

6. The classification apparatus according to claim 4, wherein the particle size selecting means controls a power supply connected to the electrodes opposed to each other to adsorb charged fine particles having particle sizes smaller than a predetermined particle size to the electrode.

7. The classification apparatus according to claim 1, further comprising a smaller-size particle discharge portion having a discharge port provided in the other electrode or its vicinity on the downstream side in the sheath gas flow for discharging charged fine particles having particle sizes smaller than a predetermined particle size but having not been adsorbed to the electrode together with part of the sheath gas through the discharge port.

8. The classification apparatus according to claim 7, wherein the particle size selecting means controls the flow rate of a pump connected downstream of the smaller-size particle discharge portion to control the particle size of fine particles to be discharged.

9. The classification apparatus according to claim 1, further comprising a pair of converging electrodes provided to be opposed to each other in an area between the classification region and the outlet to generate an electric field opposite in direction to that generated by the electrodes for forming the classification region to converge classified charged fine particles and lead them to the outlet.

10. The classification apparatus according to claim 1, further comprising an outlet slit provided between the converging electrodes and the outlet to selectively discharge charged fine particles converged by the converging electrodes together with part of the sheath gas and lead them to the outlet.

11. A fine particle measuring apparatus comprising:
    the classification apparatus according to claim 1; and
    a detector provided downstream of the outlet for detecting the number of the remaining charged fine particles contained in the sheath gas introduced thereinto.

12. The fine particle measuring apparatus according to claim 11, wherein the detector is a Faraday cup electrometer.

13. The fine particle measuring apparatus according to claim 11, further comprising a data processing unit which retains the previously-determined charging rate of an aerosol as a measuring object and calculates the fine particle number concentration of the measured aerosol based on the quantity of electricity measured by the detector.

* * * * *